US00PP37173P3

(12) United States Plant Patent
Beatson

(10) Patent No.: US PP37,173 P3
(45) Date of Patent: Dec. 23, 2025

(54) HOP PLANT NAMED 'NZH-3077'

(50) Latin Name: ***Humulus lupulus* L.**
Varietal Denomination: NZH-3077

(71) Applicant: NEW ZEALAND HOPS LIMITED, Nelson (NZ)

(72) Inventor: Ronald Alan Beatson, Motueka (NZ)

(73) Assignee: NEW ZEALAND HOPS LIMITED, Appleby (NZ)

( * ) Notice: Subject to any disclaimer, the term of this patent is extended or adjusted under 35 U.S.C. 154(b) by 0 days.

(21) Appl. No.: 19/195,758

(22) Filed: May 1, 2025

(65) Prior Publication Data

US 2025/0344620 P1 Nov. 6, 2025

Related U.S. Application Data

(60) Provisional application No. 63/642,059, filed on May 3, 2024.

(51) Int. Cl.
*A01H 5/02* (2018.01)
*A01H 5/10* (2018.01)
*A01H 6/28* (2018.01)

(52) U.S. Cl.
USPC ..... Plt./258
CPC ..... *A01H 6/28* (2018.05); *A01H 5/10* (2013.01)

(58) Field of Classification Search
USPC ..... Plt./258
See application file for complete search history.

(56) References Cited

U.S. PATENT DOCUMENTS

PP26,882 P3 * 6/2016 Puterbaugh ..... A01H 6/00 Plt./356.21

* cited by examiner

*Primary Examiner* — Karen M Redden
(74) *Attorney, Agent, or Firm* — Panitch Schwarze Belisario & Nadel LLP; Stephany G. Small; Travis W. Bliss

(57) ABSTRACT

The new hop plant variety 'NZH-3077' is provided. The new variety was produced by open pollination of 'Riwaka' (female parent, not patented) in the course of a planned breeding program. 'NZH-3077' is characterised by having large cones with medium compactness which are early-season maturing. 'NZH-3077' may be used for brewing purposes.

3 Drawing Sheets

CROSS REFERENCE TO RELATED APPLICATIONS

This application claims priority to U.S. Provisional Patent Application No. 63/642,059, which was filed on May 3, 2024, the contents of which are hereby incorporated by reference for all purposes.

Latin name of genus and species of plant claimed: *Humulus lupulus* L.

Variety denomination: 'NZH-3077'.

BACKGROUND OF THE INVENTION

The new variety of hop, *Humulus lupulus* L., of the present invention was created in the course of a planned breeding program carried out at Motueka, New Zealand. It was selected from a population of triploid seedlings derived from the open pollination of 'Riwaka' (the female parent, i.e. the seed parent; not patented) The new variety was produced by open pollination of 'Riwaka'.

The cross was carried out in January 2017. The seeds resulting from the above cross were germinated and the seedlings were then raised and planted in a field at Motueka, New Zealand in November 2017. The seedlings remained in the field for the 2017-2018 and 2018-2019 seasons to allow for agronomic, sensory, and chemistry traits to be measured and/or assessed. Selective study resulted in the identification of a single plant of the new variety from the population of seedlings derived from the above open pollination of 'Riwaka'.

During the 2019 season the new variety was clonally propagated using soft tip methods and 15 rooted cutting plants were potted. The resulting plants were found to be true to type demonstrating that the characteristics of the new variety are stable and strictly transmitted by asexual propagation from one generation to another. Further plants of the new variety were asexually propagated and a trial plot was planted in 2021-2022.

SUMMARY OF THE INVENTION

It was found that the new variety of hop plant of the present invention is characterised by having large cones with medium compactness which are early-season maturing.

The new variety of the present invention can readily be distinguished from its ancestors. More specifically, 'Riwaka' (i.e., the female parent) displays a medium number of cones on the side shoots from the upper third of the plant compared to the new variety, which displays very many cones on the side shoots from the upper third of the plant. The new variety also has a large cone size compared to a medium cone size for 'Riwaka'. Moreover, the new variety can be readily distinguished from other similar non-parental varieties. For example, when compared to '94-21-19' (not patented), the new variety has a high head volume compared to the very high volume of head for '94-21-19'.

The new variety has been named 'NZH-3077'. The new variety was previously named L17.023-077. L17.023-077 has also been referred to as the Breeder Code for the new variety.

BRIEF DESCRIPTION OF THE DRAWINGS

The accompanying photographs show as nearly true as it is reasonably possible to make the same, in a color illustration of this character, typical specimens of the new variety. The illustrated plants were approximately three years old.

DETAILED BOTANICAL DESCRIPTION

Figure 1:
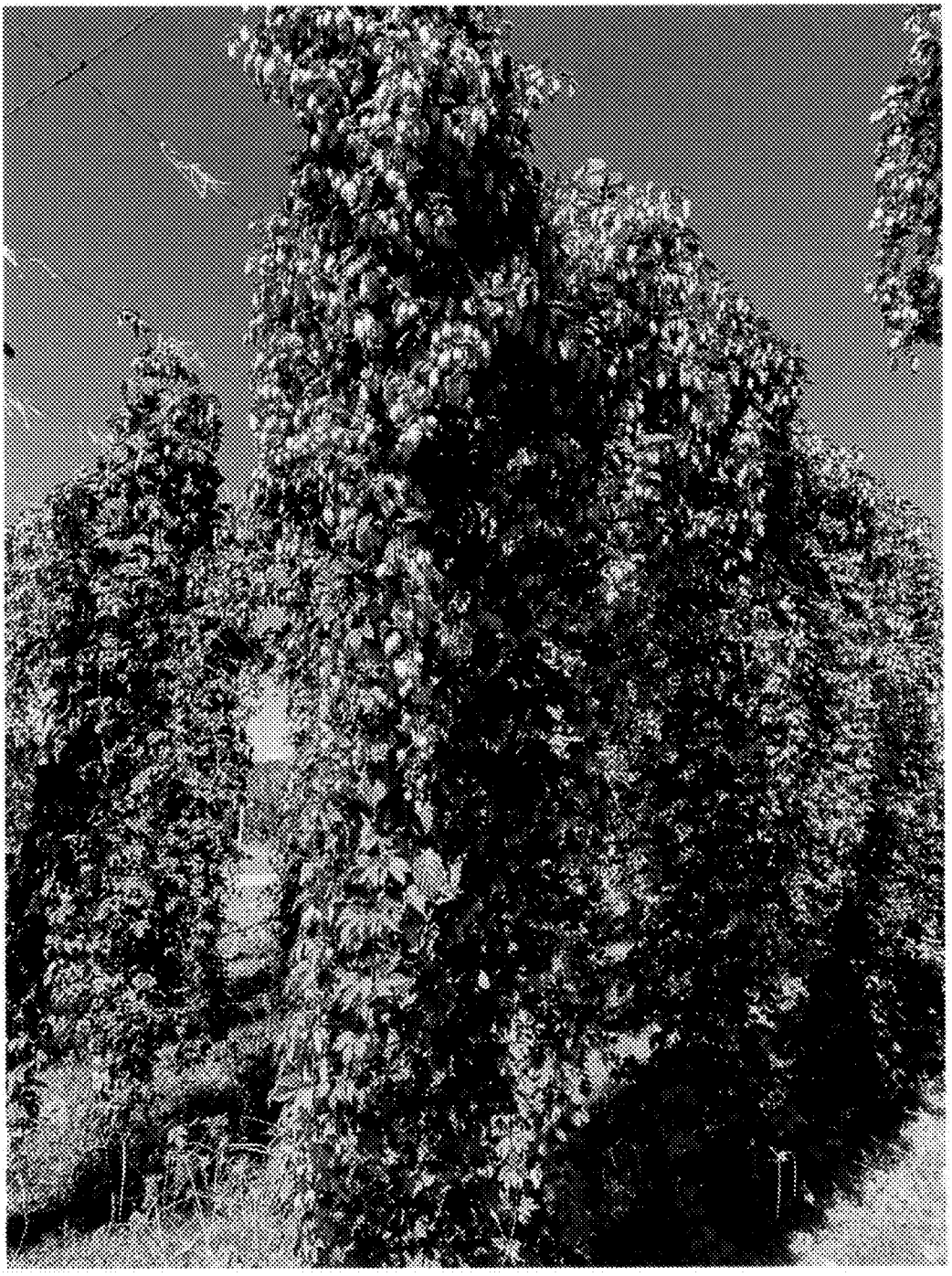
FIG. 1 illustrates a specimen of the 'NZH-3077' plant growing outdoors.
Figure 2:
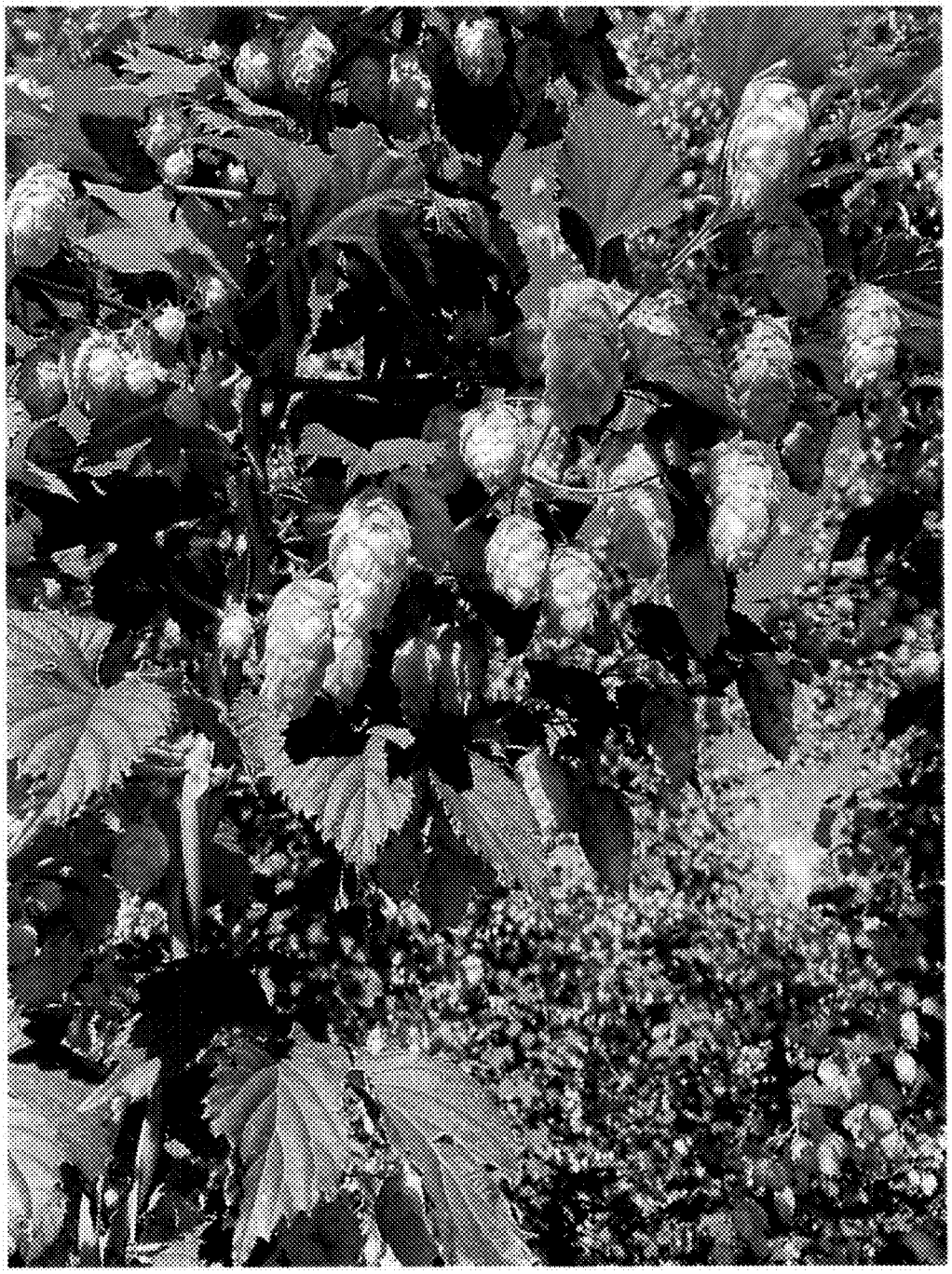
FIG. 2 illustrates a close-up view of a specimen of the 'NZH-3077' plant growing outdoors.
Figure 3:
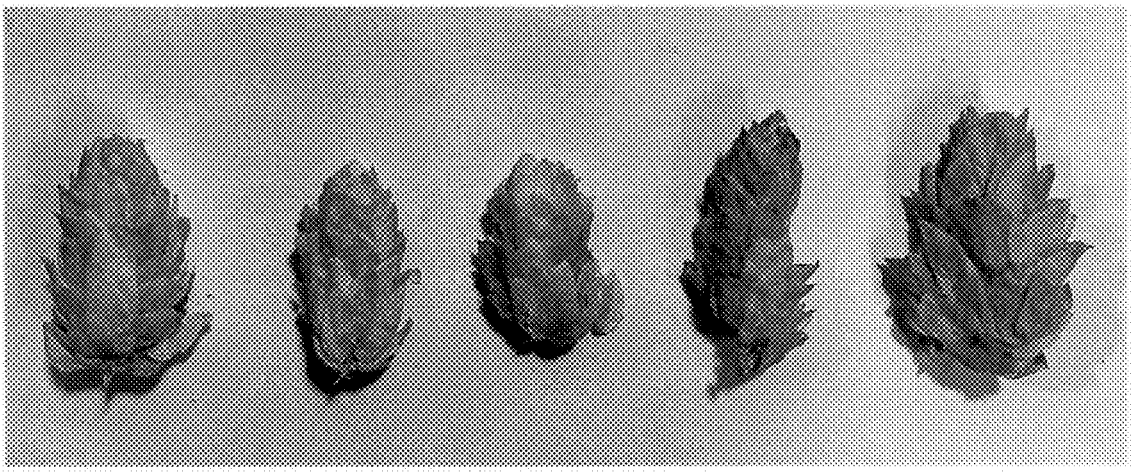
FIG. 3 illustrates specimens of 'NZH-3077' dried cones.

The chart used in the identification of colors is that of The Royal Horticultural Society (The R.H.S. Colour Chart, 2001 edition). The terminology which precedes reference to the chart has been added to indicate the corresponding color in more common terms and The R.H.S. Colour Chart designation herein represents the closest color observed on the majority of the specified botanical features. The description is based on two to three-year-old specimens of the new variety, observed during the 2024-2025 season while growing in Motueka, New Zealand.

Botanical classification: *Humulus lupulus* L. cultivar 'NZH-3077'.

Commercial classification: Hop Plant.

Chemical characteristics:

TABLE 1

| Compound | Percentage |
|---|---|
| Alpha acid | 6.4% |
| Beta acid | 4.0% |
| Cohumulone content (as % of Alpha acids) | 39.5% |
| Humulene | 5.2% |
| Farnesene | 8.4% |
| humulene caryophyllene ratio | 1.79:1 |

Plant:

*Growth type*.—Normal.

*Shape club*.—Shaped.

*Volume of head*.—80 cm in diameter and 150 cm in length.

*Productivity*.—Average yield is 1.6 tonnes/ha.

*Use*.—Primarily flavoring and bittering ingredient for beer.

*Harvest date*.—Early (commencing early March) in Motueka, New Zealand, under normal conditions.

Main shoot:

*Anthocyanin coloration*.—Weak.

*Background color of upper half*.—Yellow-Green Group 151C.

*Intensity of color*.—Medium.

*Stripe*.—Present.

*Stripe color*.—Yellow-Green Group 151C.

*Node pubescence*.—Weak.

*Vine diameter*.—Width at base is approximately 12.02 mm on average; width halfway up vine is approximately 11.6 mm on average.

*Vine length*.—Approximately 5.0 m on average.

*Internode length*.—Medium; approximately 57.7 cm on average.

*Thorns*.—Present.

*Number of thorns*.—Very few.

*Anthocyanin coloration of thorns*.—Weak.

*Thorn color*.—Green-Yellow Group 1D.

Lateral shoots:

*Side shoot from middle third of plant*.—Length: long; approximately 76.5 cm on average. — density of foliage: dense. — number of cones per node: many; approximately 45.3 on average. — number of nodes per lateral shoot: many; approximately 12.5 on average.

*Side shoot from upper third of plant*.—Length: long; approximately 73.5 cm on average. — density of foliage: dense. — number of cones per node: many; approximately 43.6 on average. — number of nodes per lateral shoot: many; approximately 38.3 on average.

*Distribution of lateral shoots*.—Predominantly top third of plant.

*Attitude of lateral shoots*.—Spreading.

Leaves:

*Size*.—Large; length is approximately 128.3 mm on average; width is approximately 134.6 mm on average.

*Arrangement*.—Opposite.

*Blistering of upper side of blade*.—Weak.

*Color*.—Upper surface is Green Group 141B.

*Intensity of green color of upper side of blade*.—Medium.

*Glossiness of upper surface*.—Absent or very weak.

*Lobes*.—Present.

*Number of lobes*.—Five.

*Leaf margin*.—Dentate.

*Basal sinus*.—Medium with a shallow depth.

*Lateral sinus*.—Medium.

*Spines on midrib of under surface*.—Number: absent or very few. — shape: straight.

*Venation*.—Palmate with a color of Greyed-Green Group 191B.

*Petiole*.—Length: approximately 103.35 mm on average. — width: approximately 3.6 mm on average. — color: Red-Purple Group 61B.

*Stipule*.—Pose: drooping. — size: medium; length is approximately 17.93 mm on average; width is approximately 10.5 mm on average. — shape: triangular. — color: Greyed-Green Group 192A.

Inflorescence:

Flowering:

*Commencement of flowering*.—Medium (December in Motueka, New Zealand).

Cone:

*Length*.—Large; approximately 48.7 mm on average.

*Shape of longitudinal section*.—Narrow ovate.

*Shape of cross section*.—Square.

*Green weight* (*average over* 100).—Low with a range of between 51.0 g to 100.0 g.

*Compactness*.—Medium.

*Strig*.—Length: medium; approximately 40.6 mm on average. — width: thin; approximately 3.7 mm on average. — number of nodes: medium; approximately 14.4 on average. — anthocyanin: absent. — color: Greyed-Green Group 191D.

*Bract*.—Frequency: medium. — size: medium to large; length is approximately 17.8 mm on average; width is approximately 11.8 mm on average. — ratio width/length: large. — apex length: short; approximately 1.6 mm on average. — color: Yellow Group 11B. — intensity of green color: medium. — tip shape: cuspidate. — tip position: oppressed.

*Bracteole*.—Color: Yellow Group 11C. — length: approximately 15.1 mm on average. — width: approximately 8.1 mm on average.

Development:

*Pest and disease*.—'NZH-3077' does not appear particularly resistant or susceptible to pests or diseases known to afflict *Humulus lupulus*.

*Hardiness*.—Zone classification not determined.

The invention claimed is:

1. A new and distinct variety of Hop plant named 'NZH-3077', substantially as illustrated and described herein.

* * * * *